(12) United States Patent
Green et al.

(10) Patent No.: US 9,997,341 B2
(45) Date of Patent: Jun. 12, 2018

(54) UNKNOWN IDENTIFICATION USING COLLISION CROSS SECTION

(71) Applicant: Micromass UK Limited, Wilmslow (GB)

(72) Inventors: Martin Raymond Green, Bowdon (GB); Kevin Giles, Stockport (GB); Keith Richardson, Derbyshire (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days. days.

(21) Appl. No.: 15/125,350

(22) PCT Filed: Mar. 10, 2015

(86) PCT No.: PCT/GB2015/050701
§ 371 (c)(1),
(2) Date: Sep. 12, 2016

(87) PCT Pub. No.: WO2015/136272
PCT Pub. Date: Sep. 17, 2015

(65) Prior Publication Data
US 2017/0250062 A1    Aug. 31, 2017

(30) Foreign Application Priority Data

Mar. 10, 2014 (EP) .................................. 14158643
Mar. 10, 2014 (GB) .................................. 1404195.8

(51) Int. Cl.
*H01J 49/00* (2006.01)
*G01N 27/62* (2006.01)

(52) U.S. Cl.
CPC ........ *H01J 49/0036* (2013.01); *G01N 27/622* (2013.01); *H01J 49/005* (2013.01); *H01J 49/0031* (2013.01)

(58) Field of Classification Search
CPC .. G01N 27/622; H01J 49/0036; H01J 49/005; H01J 49/0027; H01J 49/0081; H01J 49/02
(Continued)

(56) References Cited

U.S. PATENT DOCUMENTS 6,495,824 B1   12/2002  Atkinson
6,831,273 B2   12/2004  Jenkins et al.
(Continued)

FOREIGN PATENT DOCUMENTS

WO    2004/012231    2/2004
WO    2010/102291    9/2010

OTHER PUBLICATIONS

Lapthorn et al., "Ion Mobility Spectrometry-Mass Spectrometry (IMS-MS) of Small Molecules: Separating and Assigning Structures to Ions", Mass Spectrometry Reviews, vol. 32, No. 1, p. 43-71, Aug. 2012.
(Continued)

*Primary Examiner* — Nicole Ippolito

(57) ABSTRACT

A method of mass spectrometry is disclosed comprising experimentally determining or measuring one or more first ion mobility values, collision cross sections or interaction cross sections collision cross sections or first ion mobility parameters and one or more mass or mass to charge ratios of one or more analyte ions, generating a first list of possible candidate compounds which correspond to said one or more analyte ions on the basis of the one or more determined or measured masses or mass to charge ratios, and calculating, estimating or determining one or more second ion mobility values, collision cross sections or interaction cross sections collision cross sections or second ion mobility parameters of at least some of the candidate compounds in the first list. The method further comprises a step of either: (i) generating a
(Continued)

second reduced list of possible candidate compounds by filtering or removing candidate compounds from the first list if the difference between said one or more experimentally determined or measured first ion mobility values, collision cross sections or interaction cross sections collision cross sections or first ion mobility parameters and the one or more calculated, estimated or determined second ion mobility values, collision cross sections or interaction cross sections collision cross sections or second ion mobility parameters is greater than a predetermined amount; and/or (ii) reducing a likelihood value associated with one or more possible candidate compounds in the first list if the difference between said one or more experimentally determined or measured first ion mobility values, collision cross sections or interaction cross sections collision cross sections or first ion mobility parameters and the one or more calculated, estimated or determined second ion mobility values, collision cross sections or interaction cross sections collision cross sections or second ion mobility parameters is greater than a predetermined amount.

20 Claims, 2 Drawing Sheets

(58) Field of Classification Search
USPC .................................. 250/281, 282, 283, 290
See application file for complete search history.

(56) References Cited

U.S. PATENT DOCUMENTS

| | | | |
|---|---|---|---|
| 7,812,305 | B2 | 10/2010 | Miller et al. |
| 8,242,442 | B2 | 8/2012 | Krueger et al. |
| 8,278,620 | B2 | 10/2012 | Schwartz et al. |
| 8,384,024 | B2 | 2/2013 | Miller et al. |
| 8,525,106 | B2 | 9/2013 | Muntean |
| 8,618,477 | B2 | 12/2013 | Krueger et al. |
| 8,921,778 | B2 | 12/2014 | Atkinson et al. |
| 2007/0114382 | A1 | 5/2007 | Clemmer et al. |
| 2010/0108877 | A1 | 5/2010 | Wu et al. |
| 2010/0224770 | A1 | 9/2010 | Burns et al. |
| 2013/0009053 | A1 | 1/2013 | Wu |
| 2013/0218478 | A1* | 8/2013 | Campuzano ......... G01N 27/622 702/23 |
| 2014/0252218 | A1* | 9/2014 | Wright ............... H01J 49/0036 250/282 |
| 2016/0054264 | A1 | 2/2016 | Carver et al. |

OTHER PUBLICATIONS

Knapman T W et al., "Considerations in Experimental and Theoretical Collision Cross-Section Meansurements of Small Molecules Using Travelling Wave Ion Mobility Spectrometry-Mass Spectrometry", International Journal of Mass Spectrometry, Elsevier Science Publishers, vol. 298, No. 1-3, p. 17-23, Dec. 2010.

Shvartsburg et al., "An Exact Hard-Spheres Scattering Model for the Mobilities of Polyatomic Ions", Chemical Physics Letters, p. 86-91 Oct. 1996.

Bush et al., "Collision Cross Sections of Proteins and Their Complexes: a Calibration Framework and Database for Gas-Phase Structural Biology" Analytical Chemistry, vol. 82, No. 22, p. 9557-9565, Nov. 2010.

Dwivedi et al., "Rapid Resolution of Carbohydrate Isomers by Electrospray Ionization Ambient Pressure Ion Mobility Spectrometry-Time-of-Flight Mass Spectrometry (ESI-APIMS-TOFMS)", Focus: From Mobilities to Proteomes, p. 1163-1175, Apr. 2007.

Fernandez-Maestre et al., "Buffer Gas Modifiers Effect Resolution in Ion Mobility Spectrometry Through Selective Ion-Molecule Clustering Reactions", Rapid Communications in Mass Spectrometry, vol. 26, No. 19, p. 2217-2222, Sep. 2012.

Fernandez-Maestre et al., "Using a Buffer Gas Modifier to Change Separation Selectivity in Ion Mobility Spectrometry", Journal of Mass Spectrometry, vol. 298, No. 1-3, p. 2-9, Dec. 2010.

Green et al., "Modification of Ion Mobility Separation Using Volatile Organic Dopants on a Quadrupole-Ion Mobility-Orthogonal Time-Of-Flight Mass Spectrometer", Proceedings 59th ASMS, 2011.

Williams et al., Use of Ion Mobility Mass Spectrometry and a Collision Cross-Section Algorithm to Study an Organometallic Ruthenium Anticancer Complex and its Adducts with a DNA.

* cited by examiner

UNKNOWN IDENTIFICATION USING COLLISION CROSS SECTION

CROSS REFERENCE TO RELATED APPLICATIONS

This application is the National Stage of International Application No. PCT/GB2015/050701, filed 10 Mar. 2015 which claims priority from and the benefit of United Kingdom patent application No. 1404195.8 filed on 10 Mar. 2014 and European patent application No. 14158643.8 filed on 10 Mar. 2014. The entire contents of these applications are incorporated herein by reference.

FIELD OF THE INVENTION

The present invention generally relates to mass spectrometry and in particular to methods of mass spectrometry and mass spectrometers.

BACKGROUND

Mass spectrometry ("MS") and tandem mass spectrometry ("MS-MS") are well established methods of identifying unknown compounds. Exact mass measurement of molecular ions and/or fragment ions can give information as to the possible elemental composition and functional groups present in an unknown compound. Matching of mass spectra with library spectra can help to identify compounds or identify structurally related compounds. This information coupled with other techniques such as optical spectroscopy or NMR etc. can give a high degree of specificity in compound identification. However, these methods alone can often result in ambiguity with several candidate compounds being assigned to the unknown.

It is desired to provide an improved method of mass spectrometry.

SUMMARY

According to an aspect there is provided a method of mass spectrometry comprising:

experimentally determining or measuring one or more first ion mobility values, collision cross sections or interaction cross sections and one or more mass or mass to charge ratios of one or more analyte ions;

generating a first list of possible candidate compounds which correspond to the one or more analyte ions on the basis of the one or more determined or measured masses or mass to charge ratios;

calculating, estimating or determining one or more second ion mobility values, collision cross sections or interaction cross sections of at least some of the candidate compounds in the first list; and either: (i) generating a second reduced list of possible candidate compounds by filtering or removing candidate compounds from the first list if the difference between the one or more experimentally determined or measured first ion mobility values, collision cross sections or interaction cross sections and the one or more calculated, estimated or determined second ion mobility values, collision cross sections or interaction cross sections is greater than a predetermined amount; and/or (ii) reducing a likelihood value associated with one or more possible candidate compounds in the first list if the difference between the one or more experimentally determined or measured first ion mobility values, collision cross sections or interaction cross sections and the one or more calculated, estimated or determined second ion mobility values, collision cross sections or interaction cross sections is greater than a predetermined amount.

An embodiment relates to a method of mass spectrometry in which the collision or interaction cross sections and the masses or mass to charge ratios of one or more analyte ions are experimentally determined or measured, and a first list of possible candidate compounds is compiled based on the determined or measured masses or mass to charge ratios. A collision or interaction cross section may then be theoretically calculated, estimated or determined for each candidate compound in the first list. The theoretically calculated, estimated or determined collision or interaction cross sections is then used to filter or remove candidate compounds from the first list or to reduce a likelihood value associated with one or more of the candidate compounds in the first list.

In this way, confidence in the identification of the compounds can advantageously be increased. By theoretically calculating, estimating or determining collision cross sections in this manner it is not necessary, for example, to rely on experimentally determined collision cross section values.

Furthermore, the embodiment advantageously makes efficient use of computational power, since the collision or interaction cross section is only calculated, estimated or determined for those compounds present in the first list (i.e. which have already been identified as possible matches). This means that the calculation, estimation or determination can effectively be carried out in real-time, i.e. during the experimental work flow or experimental run.

It will be apparent therefore that an improved method of mass spectrometry is provided.

According to an embodiment, the method further comprises:

experimentally determining or measuring one or more first additional physico-chemical or other properties of the one or more analyte ions;

calculating, estimating or determining one or more second additional physico-chemical or other properties of at least some of the candidate compounds in the first list; and either: (i) generating the second reduced list of possible candidate compounds by filtering or removing candidate compounds from the first list based on the difference between the one or more experimentally determined or measured first additional physico-chemical or other properties and the one or more calculated, estimated or determined second additional physico-chemical or other; and/or (ii) reducing a likelihood value associated with one or more possible candidate compounds in the first list based on the difference between the one or more experimentally determined or measured first additional physico-chemical or other properties and the one or more calculated, estimated or determined second additional physico-chemical or other properties.

According to an embodiment, the one or more additional physico-chemical or other properties comprise peak shape, peak width, peak skew, number of peaks, and/or peak kurtosis.

According to an embodiment, the method further comprises:

ionising a sample to produce the analyte ions; or ionising a sample to produce first ions, and then fragmenting or reacting the first ions to produce the analyte ions.

According to an embodiment, the step of experimentally determining or measuring the one or more first masses or mass to charge ratios comprises mass analysing the analyte ions.

According to an embodiment, the step of experimentally determining or measuring the one or more first ion mobility values, collision cross sections or interaction cross sections comprises temporally separating at least some of the analyte ions according to their ion mobility.

According to an embodiment, the analyte ions comprise ions generated from a sample under first conditions and ions generated from the sample under second different conditions.

According to an embodiment:

the first conditions comprise one or more first pre-ionisation, ionisation and/or post-ionisation conditions; and the second different conditions comprise one or more second different pre-ionisation, ionisation and/or post-ionisation conditions.

According to an embodiment, the first and/or second conditions are selected from the group consisting of:

(i) the composition and/or concentration of a salt, dopant, derivatisation agent, reagent, shift reagent, supercharging reagent or charge reduction reagent which is added to a liquid sample prior to ionisation;

(ii) the composition and/or concentration of a neutral gas, dopant gas, derivatisation agent gas, reagent gas, shift reagent gas, supercharging reagent gas or charge reduction reagent gas which is added to a gaseous or vapour phase sample prior to ionisation;

(iii) the composition and/or concentration of a neutral gas, reactive gas, dopant gas, derivatisation agent, reagent gas, shift reagent gas, supercharging reagent gas or charge reduction reagent gas which is arranged to interact or react with analyte ions after ionisation; and (iv) the composition and/or concentration of dopant ions, derivatisation ions, reagent ions, supercharging reagent ions or charge reduction reagent ions which are arranged to interact or react with analyte ions after ionisation.

According to an embodiment, the first and/or second conditions are selected from the group consisting of: (i) a condition that affects a charge state of the analyte ions; (ii) a condition that affects an energy level of the analyte ions; (iii) a condition that affects the kinetic energy of the analyte ions; (iv) a condition that affects an activation energy of the analyte ions; and (v) a condition that affects the conformational form or nature of the analyte ions.

According to an embodiment, the first and/or second conditions are selected from the group consisting of: (i) an ionisation condition of an ion source; (ii) the type of ion source used to ionise a sample; (iii) a voltage setting of an ion source; (iv) an ionisation polarity of ions being generated by an ion source; (v) a flow rate of sample supplied to an ion source; (vi) one or more liquid chromatography conditions of a liquid chromatography system; (vii) a composition of a liquid chromatography solution or solvent; and (viii) a liquid chromatography flow rate.

According to an embodiment, the first and/or second conditions are selected from the group consisting of: (i) subjecting ions to hydrogen deuterium exchange; (ii) one or more hydrogen deuterium exchange conditions; (iii) subjecting ions to activation, photo-activation, dissociation or photo-dissociation; (iv) one or more dissociation, photo-dissociation, activation, and/or photo-activation conditions; (v) subjecting ions to heating or RF heating; (vi) one or more heating or RF heating conditions; (vii) subjecting ions to electromagnetic radiation, microwave radiation or laser irradiation; (viii) one or more electromagnetic radiation, microwave radiation or laser irradiation conditions; (ix) subjecting ions to fragmentation or reaction; and (x) one or more fragmentation or reaction conditions.

According to an embodiment, the step of calculating, estimating or determining the one or more second ion mobility values, collision cross sections or interaction cross sections of at least some of the candidate compounds in the first list comprises calculating the one or more second ion mobility values, collision cross sections or interaction cross sections taking into account the first conditions and/or the second conditions.

According to an embodiment, the method further comprises:

determining a first ion mobility value, collision cross section or interaction cross section difference between the first ion mobility values, collision cross sections or interaction cross sections determined or measured for the ions generated from the sample under the first conditions and the ions generated from the sample under the second different conditions;

determining a second ion mobility value, collision cross section or interaction cross section difference between the second ion mobility values, collision cross sections or interaction cross sections calculated, estimated or determined for the ions generated from the sample under the first conditions and the ions generated from the sample under the second different conditions; and either: (i) generating the second reduced list of possible candidate compounds by filtering or removing candidate compounds from the first list based on the difference between the first ion mobility value, collision cross section or interaction cross section difference and the second ion mobility value, collision cross section or interaction cross section difference; and/or (ii) reducing a likelihood value associated with one or more possible candidate compounds in the first list based on the difference between the first ion mobility value, collision cross section or interaction cross section difference and the second ion mobility value, collision cross section or interaction cross section difference.

According to an embodiment:

the step of experimentally determining or measuring the one or more first ion mobility values, collision cross sections or interaction cross sections comprises experimentally determining or measuring a first ion mobility value, collision cross section or interaction cross section of at least some of the analyte ions under first experimental conditions, and experimentally determining or measuring a first ion mobility value, collision cross section or interaction cross section of at least some of the analyte ions under second different experimental conditions; and/or the step of experimentally determining or measuring the one or more mass or mass to charge ratios comprises experimentally determining or measuring a mass or mass to charge ratio of at least some of the analyte ions under first experimental conditions, and experimentally determining a mass or mass to charge ratio of at least some of the analyte ions under second different experimental conditions.

According to an embodiment, the first experimental conditions and/or the second experimental conditions are selected from the group consisting of: (i) a voltage applied to an ion-optical component; (ii) a route taken by analyte ions through a portion of the mass spectrometer; (iii) the transit time of analyte ions through a portion of the mass spectrometer; (iv) one or more pressures within the mass spectrometer; (v) one or more temperatures within the mass spectrometer; (vi) the composition of a gas within the mass spectrometer; and (vii) the strength of an electric filed within the mass spectrometer.

According to an embodiment, the first experimental conditions and/or the second experimental conditions are selected from the group consisting of: (i) the composition of an ion mobility separation or buffer gas; (ii) the composition of one or more additives, one or more dopants and/or one or more reagents added to an ion mobility separation or buffer gas; (iii) the flow rate and/or direction of an ion mobility separation or buffer gas; (iv) the pressure or number density of an ion mobility separation or buffer gas; (v) the temperature within an ion mobility separation device; (vi) the strength of an electric field within an ion mobility separation device; (vii) the path length traveled by ions within an ion mobility separation device; (viii) the residence time of ions within an ion mobility separation device; (ix) the initial width of an ion pulse introduced into an ion mobility separation device; and (x) the speed, amplitude or repeat pattern of a travelling DC wave within an ion mobility separation device.

According to an embodiment, the step of calculating, estimating or determining the one or more second ion mobility values, collision cross sections or interaction cross sections of at least some of the candidate compounds in the first list comprises calculating the one or more second ion mobility values, collision cross sections or interaction cross sections taking into account the first experimental conditions and/or the second experimental conditions.

According to an embodiment, the method further comprises:

determining a first ion mobility value, collision cross section or interaction cross section difference between the first ion mobility value, collision cross section or interaction cross section determined or measured under the first experimental conditions and the first ion mobility value, collision cross section or interaction cross section determined or measured under the second experimental conditions;

determining a second ion mobility value, collision cross section or interaction cross section difference between a second ion mobility value, collision cross section or interaction cross section calculated, estimated or determined using the first experimental conditions and a second ion mobility value, collision cross section or interaction cross section calculated, estimated or determined using the second experimental conditions; and either: (i) generating the second reduced list of possible candidate compounds by filtering or removing candidate compounds from the first list based on the difference between the first ion mobility value, collision cross section or interaction cross section difference and the second ion mobility value, collision cross section or interaction cross section difference; and/or (ii) reducing a likelihood value associated with one or more possible candidate compounds in the first list based on the difference between the first ion mobility value, collision cross section or interaction cross section difference and the second ion mobility value, collision cross section or interaction cross section difference.

According to an embodiment, the step of generating the first list of possible candidate compounds which correspond to the one or more analyte ions on the basis of the one or more determined or measured masses or mass to charge ratios comprises using a library search to generate the first list of possible candidate compounds.

According to an embodiment, the step of generating the first list of possible candidate compounds which correspond to the one or more analyte ions on the basis of the one or more determined or measured masses or mass to charge ratios comprises matching one or more of the one or more determined or measured masses or mass to charge ratios to one or more library masses of mass to charge ratios.

According to an embodiment, the step calculating, estimating or determining the one or more second ion mobility values, collision cross sections or interaction cross sections comprises:

calculating a three dimensional structure of at least some of the candidate compounds in the first list; and calculating one or more of the one or more second ion mobility values, collision cross sections or interaction cross sections using the three dimensional structure.

According to an embodiment, the step of calculating, estimating or determining the one or more second ion mobility values, collision cross sections or interaction cross sections comprises calculating the effects of electronic interactions of ions with a polar or polarisable ion mobility separation or buffer gas.

According to an aspect there is provided a mass spectrometer comprising:

apparatus arranged and adapted to experimentally determine or measure one or more first ion mobility values, collision cross sections or interaction cross sections and one or more mass or mass to charge ratios of one or more analyte ions; and a control system arranged and adapted:

(i) to generate a first list of possible candidate compounds which correspond to the one or more analyte ions on the basis of the one or more determined or measured masses or mass to charge ratios;

(ii) to calculate, estimate or determine one or more second ion mobility values, collision cross sections or interaction cross sections of at least some of the candidate compounds in the first list; and either: (iii) to generate a second reduced list of possible candidate compounds by filtering or removing candidate compounds from the first list if the difference between the one or more experimentally determined or measured first ion mobility values, collision cross sections or interaction cross sections and the one or more calculated, estimated or determined second ion mobility values, collision cross sections or interaction cross sections is greater than a predetermined amount; and/or (iv) to reduce a likelihood value associated with one or more possible candidate compounds in the first list if the difference between the one or more experimentally determined or measured first ion mobility values, collision cross sections or interaction cross sections and the one or more calculated, estimated or determined second ion mobility values, collision cross sections or interaction cross sections is greater than a predetermined amount.

According to an embodiment a theoretically calculated collision cross section ("CCS") or interaction cross section for a candidate compound structure identified by mass spectrometry is compared to the measured collision cross section or interaction cross section from ion mobility and is used to filter a candidate list of possible compounds to add specificity to the identification of the unknown.

A list of candidate structures may be generated from mass spectral data and then filtered or ranked based on a comparison of theoretically calculated collision cross section ("CCS") with measured collision cross section ("CCS"). This adds a high degree of specificity to the elucidation of unknown compounds based on MS and ion mobility data.

The embodiment represents an improvement to the known methods in which the collision cross section ("CCS") of target ions must be experimentally measured using pure synthesized standards of these targets. The experimental data is then used to confirm the presence of a target compound in a mixture.

The embodiment advantageously allows theoretical collision cross section ("CCS") or relative collision cross section ("CCS") measurements to be used to confirm unknown compound identity without requiring standards of all the possible proposed structures to be synthesized and measured.

According to an aspect there is provided a method of mass spectrometry comprising:

(a) analysing ions of an analyte or derived from an analyte using mass spectrometry and ion mobility under one or more different conditions to produce mass to charge ratio and measured collision cross section information;

(b) based on at least the mass to charge ratio information including proposed elemental composition fragmentation pattern and library search output produce a candidate list of compounds proposed for the identity of the analyte;

(c) calculating, in silico, possible three dimensional structures for each of the proposed candidates including isomeric structures for all possible ions which can be formed from the candidate compounds;

(d) calculating, in silico, the collision cross section or interaction cross section for each of the structures; and (e) filtering the candidate list based on the calculated collision cross section to provide more specific identification of the analyte.

The difference in theoretical collision cross section of the analyte under two or more physicochemical conditions may be compared with the experimentally determined collision cross section under identical conditions to filter the candidate list.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector may selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD").

Additionally or alternatively, the chromatography detector may comprise a non-destructive chromatography detector may selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenylanthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl;

(xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

Figure 1:
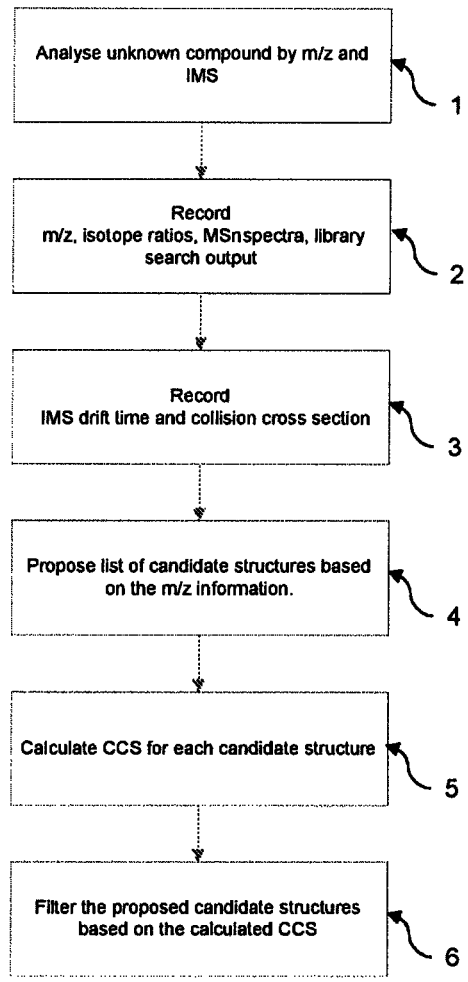
FIG. 1 shows a flow diagram illustrating an embodiment.

An embodiment is directed to a method in which one or more first ion mobility values, collision cross sections or interaction cross sections and one or more mass or mass to charge ratios of one or more analyte ions are experimentally determined or measured, and a first list of possible candidate compounds which correspond to the one or more analyte ions is generated on the basis of the one or more determined or measured masses or mass to charge ratios.

One or more second ion mobility values, collision cross sections or interaction cross sections of at least some of the candidate compounds in the first list may then be theoretically calculated, e.g. by using the control system of the mass spectrometer and may during the experimental workflow or run, and a second reduced list of possible candidate compounds may be generated by filtering or removing candidate compounds from the first list based on the difference between the one or more experimentally determined or measured first ion mobility values, collision cross sections or interaction cross sections and the one or more calculated, estimated or determined second ion mobility values, collision cross sections or interaction cross sections, or a likelihood value associated with one or more possible candidate compounds in the first list is increased, reduced, or unaltered based on the difference between the one or more experimentally determined or measured first ion mobility values, collision cross sections or interaction cross sections and the one or more calculated, estimated or determined second ion mobility values, collision cross sections or interaction cross sections.

Ion mobility can yield fundamental information as to the size and shape of an ion in the gas phase giving a measurement of collision cross section ("CCS"). Given a proposed compound identity three dimensional gas phase structures may be theoretically calculated for the ions formed from the compound. Molecular mechanics and quantum chemistry modelling approaches may be employed to do this. Commercially available software such as Gaussian (www.gaussian.com) may be used to do this. According to an embodiment, these structures may be calculated for a variety of different experimental conditions, such as drift gas compositions, and for a variety of positional isomers, stero-isomers, protomers, chiral isomers, etc. from the compound. These isomers all have the same elemental composition and so are difficult to identify by mass spectrometry alone.

Once structures are proposed, the collision cross section is may calculated using software such as MobCal from Indiana University. Reference is made to: A. A. Shvartsburg and M. F. Jarrold, An Exact Hard Spheres Scattering Model for the Mobilities of Polyatomic Ions, Chem. Phys. Lett. 1996, 261, 86-91.

An approach for calculating theoretical collision cross sections for known organometallic compounds is disclosed in Rapid Commun. Mass Spectrom. 2009; 23: 3563-3569 "Use of ion mobility mass spectrometry and a collision cross-section algorithm to study an organometallic ruthenium anticancer complex and its adducts with a DNA oligonucleotide". The purpose of this paper is to understand the structure of these compounds rather than to aid identification of unknown compounds, however the methods employed to calculate theoretical collision cross section ("CCS") are applicable to and can be used in embodiments of the present disclosure.

Other approaches can be taken including estimating the effect on the measured collision cross section of long range interactions between the ion and the neutral drift gas, e.g. to in effect calculate an "interaction cross section". These effects are caused by the presence of a polarisable drift gas or drift media containing gas phase neutrals with a permanent dipole moment. The interaction of polarisable or polar neutrals with ions depends on the electronic structure of the ions (local or bulk dipole moments, etc.) which may be very specific to a given structure.

According to an embodiment the calculated collision cross section ("CCS") is compared to the measured collision cross section ("CCS") and is used to filter a candidate list of possible compounds to add specificity to the identification of the unknown compounds and/or to add additional confidence to the identification of compounds.

According to an embodiment, isomeric forms of unknown compounds may also be identified. For example, if more than one isomeric form is present, several ion mobility peaks may be experimentally produced with the same elemental composition and exact mass and often very similar fragmentation patterns. The calculated absolute or relative collision cross section ("CCS") values may may be compared to the measured collision cross section ("CCS") values and the order in which these peaks elute from an ion mobility separation device and may used to assign and relatively quantify the different isomeric forms.

According to an embodiment, the presence or absence of these isomeric forms may on its own be used to add specificity to the identification of the analyte may in conjunction with theoretical modelling.

For example, protomers (or ions containing other charge carriers which may be localized to more than one site on the ion) are another form of isomer which may be very specific to particular candidate compounds, and may be used in an embodiment to aid identification.

According to an embodiment, to add even more specificity to the method the mass to charge ratio and collision cross section ("CCS") may be measured under different conditions and the difference in calculated collision cross section ("CCS") and measured collision cross section ("CCS") compared.

According to an embodiment, an unknown compound may be analysed using two or more drift gas compositions and the difference in collision cross section ("CCS"), experimentally determined and theoretically determined, may be compared.

Polar or polarisable drift (buffer) gases, or drift gases containing polar dopants, may may be used to give drift time shifts which are very specific to a given ion structure. This is due to long range electronic interactions between the drift media and the analyte which are specific to both the electronic structure of the analyte ion and the drift media molecules.

Theoretical calculations are may used to give the absolute collision cross section ("CCS") or interaction cross section and/or the magnitude of an expected shift in apparent collision cross section ("CCS") in different drift media. This information is may used to add specificity to compound identification.

Additionally or alternatively, in an embodiment the analyte ion may be modified e.g. by altering solution and/or gas phase chemistry may to allow two or more independent measurements of mass to charge ratio and ion mobility for the same unknown compound.

According to an embodiment, for the same analyte, the collision cross section ("CCS") of a protonated ion may be very different from a sodiated ion or an ion with a different charge carrier or adduct or derivatisation modification. This change can be related to the stereochemistry or the electronic structure of the ion, and again the experimentally observed collision cross section ("CCS") difference is may compared to the theoretically calculated difference to add specificity to the identification of the unknown compound.

According to an embodiment, activation of an ion may to raise internal temperature by an arbitrary or known amount may be used to cause unfolding or transition between conformational states. In an embodiment lasers or other energy sources are may used to excite ions before and/or during ion mobility separation. The change in apparent collision cross section ("CCS") is may compared to a theoretically calculated value, e.g. at the elevated temperature, to add more specificity to analyte identification.

According to an embodiment, supercharging and/or charge reducing techniques are may used to alter the charge state of the ion, may to allow two experimental and two theoretical collision cross section ("CCS") values to be compared based on calculated candidate structures.

In some cases the same species may exist in more than one charge state. The difference in experimental and theoretically calculated collision cross section ("CCS") for candidate compounds in these charge states may may be used, in a single experiment, to filter the candidate list.

FIG. 1 shows a flow diagram representing an embodiment. In step 1 analyte ions are analysed, using e.g. mass spectrometry and ion mobility spectrometry. The analyte may be introduced to an analyser directly or via a chromatographic separation device. The mass spectrometry and ion mobility device may be separate from or form part of the same instrument, in which case a nested ion mobility-mass to charge ratio data set is may produced.

In steps 2 and 3 both mass to charge ratio and ion mobility collision cross section ("CCS") may be recorded for the unknown analyte. According to various embodiments, mass spectrometry ("MS") or tandem mass spectrometry ("MS-MS") spectral data or data with further stages of isolation and fragmentation ("MS") may be recorded.

In step 4, a list of candidate compounds may be generated using the mass to charge ratio information. This is may done by considering possible elemental compositions based on accurate mass measurements and/or one or more library search outputs. The list may contains compounds or isomers of compounds which are consistent with the mass to charge ratio information and may correspond to the unknown analyte.

Thus, according to an embodiment, one or more accurate mass or mass to charge ratio measurements are used to generate a restricted list of possible elemental compositions, which may be ranked by isotope ratio calculations (e.g. based on the proposed elemental composition). This information along with any other data (such as fragment ions intensity, accurate mass, isotope ratios, etc.) may then be fed into a library to produce the candidate structures. That is, according to an embodiment, the first list of (plausible) candidate structures may be determined using one or more accurate masses or mass to charge ratios and one or more possible elemental compositions, together with chemical knowledge, e.g. so as to predict plausible functional groups, substructures, adducts.

In step 5, for each candidate compound a theoretical collision cross section value is may calculated, may by the methods described above. In step 6, the calculated collision cross section value is then may compared to the measured collision cross section value, and the difference between these two values is may used to either filter or rank the candidate list. According to an embodiment, this may be by exclusion of compounds which have theoretical collision cross section ("CCS") significantly different from the measured collision cross section ("CCS") and/or by ordering or ranking the list of candidates by collision cross section ("CCS") alone and/or by a combination of collision cross section ("CCS") and mass to charge ratio information.

Figure 2:
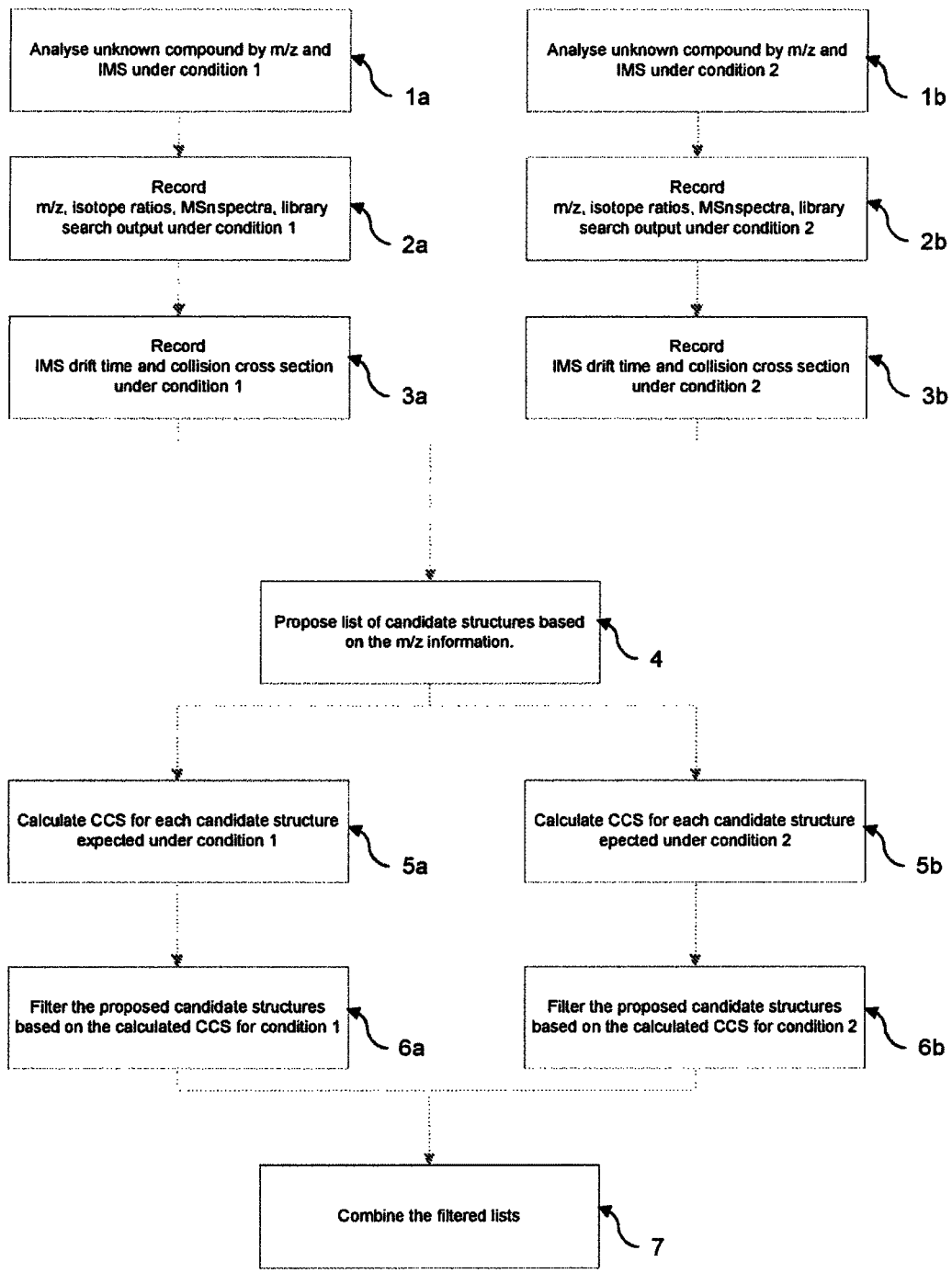
FIG. 2 shows a flow diagram illustrating a further embodiment.

FIG. 2 shows another embodiment. The embodiment of FIG. 2 is similar embodiment as shown in FIG. 1. However, in this embodiment the mass to charge ratio and collision cross section ("CCS") for the same analyte are measured under two separate known conditions. For example, according to an embodiment, the same analyte may be measured with different charge carriers and/or with a different ion mobility separation drift gas.

Thus, in steps 1a and 1b, a compound is may analysed, may under two or more different pre-ionisation, ionisation, post-ionisation and/or experimental or measurement conditions. In steps 2a, 2b, 3a, and 3b two or more sets of mass to charge ratio and collision cross section ("CCS") data are may recorded, and candidate compounds are may proposed based on the mass to charge ratio data (step 4).

Theoretical collision cross section ("CCS") under these two different conditions may be calculated in steps 5a and 5b, and may be compared to the measured collision cross section ("CCS") values under the corresponding condition. These two values may then be used to filter or rank the candidate compound list in steps 6a and 6b, as described above. The final filtered list is produced in step 7.

In various embodiments, once a theoretical collision cross section or interaction cross section has been calculated for a given ion structure under a given set of conditions it may be added to a database of theoretical cross sections and used to screen candidate structures without the need for recalculation of the theoretical collision cross section ("CCS") or interaction cross section.

In an embodiment, a mass or mass to charge ratio difference and/or an ion mobility, collision cross section or interaction cross section difference between ions generated or measured under, different analytical conditions may be used to filter or rank the first list. In particular, according to an embodiment the drift time difference of analyte ions which are caused to separate temporally in the presence of buffer gases which have different compositions may be measured and calculated, and used to filter or rank the first list. This approach according to an embodiment is particularly advantageous in that it is substantially more robust to changes in the conditions of the ion mobility separator than utilising an absolute drift time measurement. As a result, the approach according to this embodiment results in a significant improvement in precision and accuracy.

According to an embodiment, one or more additional physico-chemical or other properties of the one or more analyte ions, such as ion mobility peak shape, ion mobility peak width, ion mobility peak skew, number of ion mobility peaks and/or ion mobility peak kurtosis, may also be calculated and experimentally determined or measured in a corresponding manner to that described above, and may used to filter the first list or to alter one or more likelihood values. For example, the shape and number of ion mobility peaks associated with each analyte ion may be used e.g. to aid characterisation. This may be used in techniques such as hydrogen-deuterium exchange, where the (mass to charge ratio) isotope pattern may be compared between deuterated and non deuterated samples to work out how may exchangeable hydrogen atoms are in the sample.

In an embodiment, properties of one or more experimentally determined or measured ion peaks, such as a width, skew or kurtosis, may be determined, e.g. using a peak shape fitting. The corresponding theoretical values may be calculated, e.g. by factoring in the device parameters and conditions (resolution, etc.) into the calculations, may so as to determine one or more expected peak shapes.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   experimentally determining or measuring one or more first ion mobility values, collision cross sections or interaction cross sections and one or more mass or mass to charge ratios of one or more analyte ions;
   generating a first list of possible candidate compounds which correspond to said one or more analyte ions on the basis of said one or more determined or measured masses or mass to charge ratios;
   calculating, estimating or determining one or more second ion mobility values, collision cross sections or interaction cross sections of at least some of said candidate compounds in said first list; and
   either: (i) generating a second reduced list of possible candidate compounds by filtering or removing candidate compounds from said first list if the difference between said one or more experimentally determined or measured first ion mobility values, collision cross sections or interaction cross sections and said one or more calculated, estimated or determined second ion mobility values, collision cross sections or interaction cross sections is greater than a predetermined amount; or (ii) reducing a likelihood value associated with one or more possible candidate compounds in said first list if the difference between said one or more experimentally determined or measured first ion mobility values, collision cross sections or interaction cross sections and said one or more calculated, estimated or determined second ion mobility values, collision cross sections or interaction cross sections is greater than a predetermined amount.

2. A method as claimed in claim 1, further comprising:
   experimentally determining or measuring one or more first additional physico-chemical or other properties of said one or more analyte ions;
   calculating, estimating or determining one or more second additional physico-chemical or other properties of at least some of said candidate compounds in said first list; and
   either: (i) generating said second reduced list of possible candidate compounds by filtering or removing candidate compounds from said first list based on the difference between said one or more experimentally determined or measured first additional physico-chemical or other properties and said one or more calculated, estimated or determined second additional physico-chemical or other; or (ii) reducing a likelihood value associated with one or more possible candidate compounds in said first list based on the difference between said one or more experimentally determined or measured first additional physico-chemical or other properties and said one or more calculated, estimated or determined second additional physico-chemical or other properties.

3. A method as claimed in claim 2, wherein said one or more additional physico-chemical or other properties comprise peak shape, peak width, peak skew, number of peaks and/or peak kurtosis.

4. A method as claimed in claim 1, further comprising:
   ionising a sample to produce said analyte ions; or
   ionising a sample to produce first ions, and then fragmenting or reacting said first ions to produce said analyte ions.

5. A method as claimed in claim 1, wherein said analyte ions comprise ions generated from a sample under first conditions and ions generated from said sample under second different conditions.

6. A method as claimed in claim 5, wherein said first and/or second conditions are selected from the group consisting of:
   (i) the composition and/or concentration of a salt, dopant, derivatisation agent, reagent, shift reagent, supercharging reagent or charge reduction reagent which is added to a liquid sample prior to ionisation;
   (ii) the composition and/or concentration of a neutral gas, dopant gas, derivatisation agent gas, reagent gas, shift reagent gas, supercharging reagent gas or charge reduction reagent gas which is added to a gaseous or vapour phase sample prior to ionisation;
   (iii) the composition and/or concentration of a neutral gas, reactive gas, dopant gas, derivatisation agent, reagent gas, shift reagent gas, supercharging reagent gas or charge reduction reagent gas which is arranged to interact or react with analyte ions after ionisation; and
   (iv) the composition and/or concentration of dopant ions, derivatisation ions, reagent ions, supercharging reagent ions or charge reduction reagent ions which are arranged to interact or react with analyte ions after ionisation.

7. A method as claimed in claim 5, wherein said first and/or second conditions are selected from the group consisting of: (i) a condition that affects a charge state of said analyte ions; (ii) a condition that affects an energy level of said analyte ions; (iii) a condition that affects the kinetic energy of said analyte ions; (iv) a condition that affects an activation energy of said analyte ions; and (v) a condition that affects the conformational form or nature of said analyte ions.

8. A method as claimed in claim 5, wherein said first and/or second conditions are selected from the group consisting of: (i) an ionisation condition of an ion source; (ii) the type of ion source used to ionise a sample; (iii) a voltage setting of an ion source; (iv) an ionisation polarity of ions being generated by an ion source; (v) a flow rate of sample supplied to an ion source; (vi) one or more liquid chromatography conditions of a liquid chromatography system; (vii) a composition of a liquid chromatography solution or solvent; and (viii) a liquid chromatography flow rate.

9. A method as claimed in claim 5, wherein said first and/or second conditions are selected from the group consisting of: (i) subjecting ions to hydrogen deuterium exchange; (ii) one or more hydrogen deuterium exchange conditions; (iii) subjecting ions to activation, photo-activation, dissociation or photo-dissociation; (iv) one or more dissociation, photo-dissociation, activation, and/or photo-activation conditions; (v) subjecting ions to heating or RF heating; (vi) one or more heating or RF heating conditions; (vii) subjecting ions to electromagnetic radiation, microwave radiation or laser irradiation; (viii) one or more electromagnetic radiation, microwave radiation or laser irradiation conditions; (ix) subjecting ions to fragmentation or reaction; and (x) one or more fragmentation or reaction conditions.

10. A method as claimed in claim 5, wherein said step of calculating, estimating or determining said one or more second ion mobility values, collision cross sections or interaction cross sections of at least some of said candidate compounds in said first list comprises calculating said one or more second ion mobility values, collision cross sections or interaction cross sections taking into account said first conditions and/or said second conditions.

11. A method as claimed in claim 5, further comprising:
determining a first ion mobility value, collision cross section or interaction cross section difference between said first ion mobility values, collision cross sections or interaction cross sections determined or measured for said ions generated from said sample under said first conditions and said ions generated from said sample under said second different conditions;
determining a second ion mobility value, collision cross section or interaction cross section difference between said second ion mobility values, collision cross sections or interaction cross sections calculated, estimated or determined for said ions generated from said sample under said first conditions and said ions generated from said sample under said second different conditions; and
either: (i) generating said second reduced list of possible candidate compounds by filtering or removing candidate compounds from said first list based on the difference between said first ion mobility value, collision cross section or interaction cross section difference and said second ion mobility value, collision cross section or interaction cross section difference; or (ii) reducing a likelihood value associated with one or more possible candidate compounds in said first list based on the difference between said first ion mobility value, collision cross section or interaction cross section difference and said second ion mobility value, collision cross section or interaction cross section difference.

12. A method as claimed in claim 1, wherein:
said step of experimentally determining or measuring said one or more first ion mobility values, collision cross sections or interaction cross sections comprises experimentally determining or measuring a first ion mobility value, collision cross section or interaction cross section of at least some of said analyte ions under first experimental conditions, and experimentally determining or measuring a first ion mobility value, collision cross section or interaction cross section of at least some of said analyte ions under second different experimental conditions; and/or
said step of experimentally determining or measuring said one or more mass or mass to charge ratios comprises experimentally determining or measuring a mass or mass to charge ratio of at least some of said analyte ions under first experimental conditions, and experimentally determining a mass or mass to charge ratio of at least some of said analyte ions under second different experimental conditions.

13. A method as claimed in claim 12, wherein said first experimental conditions and/or said second experimental conditions are selected from the group consisting of: (i) a voltage applied to an ion-optical component; (ii) a route taken by analyte ions through a portion of said mass spectrometer; (iii) the transit time of analyte ions through a portion of said mass spectrometer; (iv) one or more pressures within said mass spectrometer; (v) one or more temperatures within said mass spectrometer; (vi) the composition of a gas within said mass spectrometer; and (vii) the strength of an electric filed within said mass spectrometer.

14. A method as claimed in claim 12, wherein said first experimental conditions and/or said second experimental conditions are selected from the group consisting of: (i) the composition of an ion mobility separation or buffer gas; (ii) the composition of one or more additives, one or more dopants and/or one or more reagents added to an ion mobility separation or buffer gas; (iii) the flow rate and/or direction of an ion mobility separation or buffer gas; (iv) the pressure or number density of an ion mobility separation or buffer gas; (v) the temperature within an ion mobility separation device; (vi) the strength of an electric field within an ion mobility separation device; (vii) the path length traveled by ions within an ion mobility separation device; (viii) the residence time of ions within an ion mobility separation device; (ix) the initial width of an ion pulse introduced into an ion mobility separation device; and (x) the speed, amplitude or repeat pattern of a travelling DC wave within an ion mobility separation device.

15. A method as claimed in claim 12, wherein said step of calculating, estimating or determining said one or more second ion mobility values, collision cross sections or interaction cross sections of at least some of said candidate compounds in said first list comprises calculating said one or more second ion mobility values, collision cross sections or interaction cross sections taking into account said first experimental conditions and/or said second experimental conditions.

16. A method as claimed in claim 12, further comprising:
determining a first ion mobility value, collision cross section or interaction cross section difference between said first ion mobility value, collision cross section or interaction cross section determined or measured under said first experimental conditions and said first ion mobility value, collision cross section or interaction cross section determined or measured under said second experimental conditions;
determining a second ion mobility value, collision cross section or interaction cross section difference between a second ion mobility value, collision cross section or interaction cross section calculated, estimated or determined using said first experimental conditions and a second ion mobility value, collision cross section or interaction cross section calculated, estimated or determined using said second experimental conditions; and either: (i) generating said second reduced list of possible candidate compounds by filtering or removing candidate compounds from said first list based on the difference between said first ion mobility value, collision cross section or interaction cross section difference and said second ion mobility value, collision cross section or interaction cross section difference; or (ii) reducing a likelihood value associated with one or more possible candidate compounds in said first list based on the difference between said first ion mobility value, collision cross section or interaction cross section difference and said second ion mobility value, collision cross section or interaction cross section difference.

17. A method as claimed in claim 1, wherein said step of generating said first list of possible candidate compounds which correspond to said one or more analyte ions on the basis of said one or more determined or measured masses or mass to charge ratios comprises using a library search to generate said first list of possible candidate compounds.

18. A method as claimed in claim 1, wherein said step calculating, estimating or determining said one or more second ion mobility values, collision cross sections or interaction cross sections comprises:
   calculating a three dimensional structure of at least some of said candidate compounds in said first list; and
   calculating one or more of said one or more second ion mobility values, collision cross sections or interaction cross sections using said three dimensional structure.

19. A method as claimed in claim 1, wherein said step of calculating, estimating or determining said one or more second ion mobility values, collision cross sections or interaction cross sections comprises calculating the effects of electronic interactions of ions with a polar or polarisable ion mobility separation or buffer gas.

20. A mass spectrometer comprising:
apparatus arranged and adapted to experimentally determine or measure one or more first ion mobility values, collision cross sections or interaction cross sections and one or more mass or mass to charge ratios of one or more analyte ions; and
a control system arranged and adapted to:
(i) to generate a first list of possible candidate compounds which correspond to said one or more analyte ions on the basis of said one or more determined or measured masses or mass to charge ratios;
(ii) to calculate, estimate or determine one or more second ion mobility values, collision cross sections or interaction cross sections of at least some of said candidate compounds in said first list; and
either: (iii) to generate a second reduced list of possible candidate compounds by filtering or removing candidate compounds from said first list if the difference between said one or more experimentally determined or measured first ion mobility values, collision cross sections or interaction cross sections and said one or more calculated, estimated or determined second ion mobility values, collision cross sections or interaction cross sections is greater than a predetermined amount; or (iv) to reduce a likelihood value associated with one or more possible candidate compounds in said first list if the difference between said one or more experimentally determined or measured first ion mobility values, collision cross sections or interaction cross sections and said one or more calculated, estimated or determined second ion mobility values, collision cross sections or interaction cross sections is greater than a predetermined amount.

* * * * *